United States Patent
Gross (10) Patent No.: US 9,017,078 B2
(45) Date of Patent: Apr. 28, 2015

(54) METHOD AND SYSTEM FOR IDENTIFY, TREATMENT AND WEANING FROM INTERNET AND COMPUTER ADDICTION

(76) Inventor: David Gross, Kiryat Bialik (IL)

( * ) Notice: Subject to any disclaimer, the term of this patent is extended or adjusted under 35 U.S.C. 154(b) by 162 days.

(21) Appl. No.: 13/570,289

(22) Filed: Aug. 9, 2012

(65) Prior Publication Data
US 2014/0045157 A1 Feb. 13, 2014

(51) Int. Cl.
*G09B 19/00* (2006.01)
*A61B 5/00* (2006.01)
*G06Q 10/10* (2012.01)
*G06Q 50/00* (2012.01)

(52) U.S. Cl.
CPC . *A61B 5/00* (2013.01); *G09B 19/00* (2013.01); *G06Q 10/101* (2013.01); *G06Q 50/01* (2013.01)

(58) Field of Classification Search
CPC .......... A61B 5/00; A61B 5/002; A61B 25/00; A61B 5/16; A61B 5/167
USPC .................................. 434/236, 219
See application file for complete search history.

(56) References Cited

U.S. PATENT DOCUMENTS

| | | | | |
|---|---|---|---|---|
| 5,716,273 A | * | 2/1998 | Yuen | 463/29 |
| 7,036,145 B1 | * | 4/2006 | Murphy et al. | 726/21 |
| 8,589,328 B1 | * | 11/2013 | Sharma | 706/48 |

* cited by examiner

*Primary Examiner* — Timothy A Musselman

(57) ABSTRACT

Self controlled method and system for identified, treatment and weaning from computer and Internet addiction. On one embodiment of the invention, the system analyzed user activity on the computer and while surfing the Internet, and presents results of his addictive level visually on user's interface. Supporting the whole information of addictive level to the user, give him the power to fight against the phenomena and prevent to increase it.

The user can decide whether he wants treatment and act to have it by personal actions or by involvement of third parties such as parents, therapist, support group or even a specific social website. For weaning from the addiction the system can provide positive feedbacks, special treatment and even presents and prizes if the user reduced dramatically his addictive level.

16 Claims, 10 Drawing Sheets

Fig. 6e

METHOD AND SYSTEM FOR IDENTIFY, TREATMENT AND WEANING FROM INTERNET AND COMPUTER ADDICTION

FIELD OF THE INVENTION

The present invention relates to addiction, in particular addiction of computer and Internet whether by a personal usage of a computer or on a network.

BACKGROUND OF THE INVENTION

The enormous usage of computers today, is a non separately part of human life. It can be implemented commercially by looking at the most richest companies today. These companies are from the computer industries including software and hardware manufacturing companies. These companies replaced at the last decades the traditional companies of food, oil, steel and real estate. Companies such as Microsoft™, Intel™ and IBM™ are at top of company's income lists. These companies becomes in this position because the advantages of the computer.

The advantages of the computer as a unit, has two main achievements: a better calculating tool which replaced the calculating-ruler, and a better word processing which replaced the typing machine. But the biggest achievement, which appeared at the last years, is the network. Connecting a personal computer to a network allows the user to get any information he may need from huge amount of information, which saved at companies, governments, universities and people computers and servers and other data storage. Companies such as Google™ that developed a search engine for getting the specific information the user need, is now a billion dollar company.

Although, connection to a network allows the user to be connected to users which are connected to the same network, even worldwide on a network such as the Internet. This possibility of communication between users seems to be the most powerful achievement of the computer revolution. Facebook™, the social networking company reached a half of a billion users, and the company finance value is 50 billion dollar. This data shows the great influence of social networking on economy and life. Surfing the Internet on a computer or other portable devices such as cellular phones, smart phones and the like, is an integral part of today's life at work, study and entertainment. The Internet usage can be personally or communicating socially with local friends or even with friends or colleges around the globe.

What brings the Internet to be so popular today? The answer is that there is almost no area in life that the Internet is not taking part. Starting from education, where you can find on the Internet: Encyclopedias, Dictionaries, exams, lessons, books and human knowledge, to economy where companies build websites, continuing to on-line banking and electronic shopping, to entertainment, in gaming, gambling and chat rooms, blogs, pornography, virtual words and social networks communication.

With so much information available on the Internet, easy to get and use, it is possibly the reason to use it consistently without limits. Despite so many advantages there is also a risk. Such a usage can cause users to become addicted. Addiction to the Internet can be in gaming, gambling, email, chat rooms, bogs, social networks and the like.

Recent research papers show that such an unhealthy process occurs and growing. Unhealthy usage of the computer and the Internet comes when Internet use interferes with daily life, work and relationships. One of the recent reports was published by the authors: Dr. Gwenn Schurgin O'Keefe and Dr. Kathleen Clarke-Pearson on Mar. 28, 2011 in PEDIATRICS, the Official Journal of the American Academy Of Pediatrics. The paper named: *A Clinical Report—The Impact of Social Media on Children, Adolescents, and Families*.

It deals with the Internet addiction, which can be causes by using social networks such as MySpace™, Facebook™, Twitter™, virtual words such as Second-Life™ and the Sims™, video sites such as YouTube™, blogs and gaming. It reported that using social media sites becomes a risk particularly to adolescents. Such risks as cyber bullying, online harassment, sexting and Facebook depression are affecting the mental behavior of users. According to the report, Facebook™ depression proposed as a new phenomenon, which defined as "depression that developed when preteens and teens spend a great deal of time on social media sites, such as Facebook™, and then begin to exhibit classic symptoms of depression". The report ends with a role of pediatricians to educate families about using social media safely. Achieving this goal will get more healthy children, families and society.

Another report which is presenting on the Israeli Governmental Information Technology website (www.itpolicy.gov.il/tropics_ethics/addiction) written by Helly Peretz, describes Internet addictions causes, statistics and Governmental duties fighting the addiction. It reported that 6% of 17,250 Internet users responses of an Internet survey showed that they are in a situation of Internet addiction. Over 30% of them answered that they are using the Internet to escape from reality. The average age of addicted users participating in the survey found to be 29 years old for males and 43 years old for females.

The report concluded that the Government should act to prevent Internet addiction firstly by the Educational Office to create educational learning plans. In addition, at the Law Office, laws have to be implemented to act in minimizing the risks of the addiction, for example: at work where an addictive worker can find himself losing his job, or divorce which caused by addiction of one of the couple.

The Social Office should work on a therapy process, which can take place in the existing weaning centers, or in new centers, which have to be built.

Thus, there is a need for a computerized-implemented system, acting on a personal level and having the cooperation of the user, to prevent and reduces Internet addiction.

The needed system will be used in any user's addictive level, in any age or gender. The needed system will give the user a full information of his addictive level, and have the possibility to communicate with third parties to decide which treatment needed. Third parties involvement will be according user decision or by a pre-defined status. Finally, the needed system will be acting in weaning from the addiction.

SUMMARY OF THE INVENTION

On one embodiment of the present invention, method and system are providing to help in fighting against Internet and computer addiction. It gives the user and his peripheral persons such as pediatricians, therapists, parents, friends and support group, the ability to identify the user's addiction level to the Internet and the computer. The identification stage includes analysis of user's activity. Analysis results of the addiction level are presented visually on the user interface. According to the visual results, the user can know his addictive level and can act to reduce his exposure to risk factors. These actions are self-controlled actions, which helps the user in preventing the addiction.

If the user decide to cooperate with third parties, visual results are sending via the Internet or other communication lines to third parties helping them to decide which treatment the user is needed.

According to third parties decisions, action data is sent back to user device, activating or shutting processes. These options of giving treatment or support by third parties, is helping the user in weaning from this unhealthy phenomenon.

Another embodiment of the present invention describes a method and system for identify, treatment and weaning from Internet and computer addiction, in which the decision of getting treatment and the kind of, is set automatically by a pre-defined status. A manufacturer, a user, parent, therapist, or other any kind of supervisor can activate this pre-defined status.

According to another embodiment, treatment decisions are taking place on-line by third party users, including but not limited to parent, therapist or support group.

DETAILED DESCRIPTION OF PREFERRED EMBODIMENTS

Figure 1A:
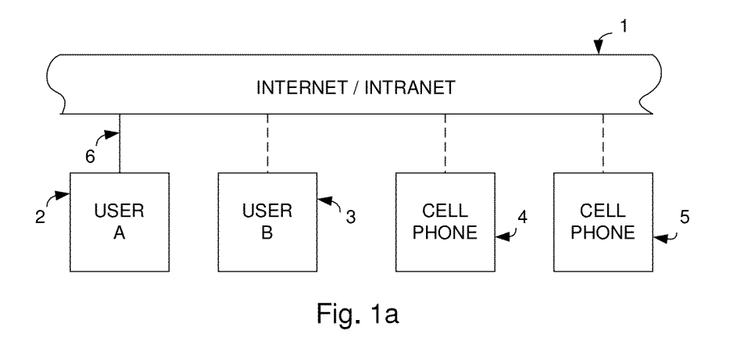
FIG. 1a is a schematic illustration depicting one embodiment of the system of the present invention.

FIG. 1a is a schematic illustration depicting one embodiment of the system of the present invention.

A network line 1 is connecting user A 2 computer and user B 3 computer with cellular phone 4 and cellular phone 5. The connection 6 between user A 2 and Internet/Intranet 1 communication line can be but not limited to LAN (local area connection) or WAN (wide area connection) including connection to World Wide Web by wireless connection or by a fixed connection.

User B 3, Cell Phone 4 or cell phone 5 can be connected to the Internet by any kind of connection, as user 2 connected or differ.

User A 2 and user B 3 comprises computers, which can vary from any kind of computer including personal computer such as: laptop, notebook, tablet or desktop or any device including an operating system and Internet capability. Cellular phone 4 comprises a system, which offer the ability to surf the Internet. On one embodiment User A 2 computer is analyzing user activity of surfing the Web.

Another embodiment of the present invention is using specific software for analyzing the activity, while in another embodiment ActiveX controls and Plug-ins may be added to a browser software program for doing the same job. Another embodiment of the present invention is using specific website which all the analyzing process is taking place including saving data and presenting results.

Results of this analysis can operate different activities to the present invention to act.

Part of those activities is sending messages and results to cell phone 4 either (or neither) to User B 3, which comprises personal computer. Parent, therapist or a friend from a support group can make a decision how to act and send an execute message or execute action to user A 2 computer to stop or delay Internet activity or any other activity.

In another embodiment of the present invention user device is not limited to be a computer device but can be a cellular phone with a network capabilities, smart phone, PDA, and can be any kind of computer for example: a desktop computer. Laptop computer, notebook computer or a website.

The system on one embodiment of the present invention can act in three modes of operation. The first one is a pre-defined option. In this mode, third parties which presenting in FIG. 1a as User B 3, Cell Phone 4 and cell phone 5 are getting involved automatically. In the second mode, User A 2 chooses to act independently against his addiction not involves any third party in the treatment and weaning process. In the third mode of operation the user chooses to involve third parties to be part of the process. Third parties can be but not limited to be parents, friends, supervisor, social websites, group therapy, therapist and doctor.

Figure 1B:
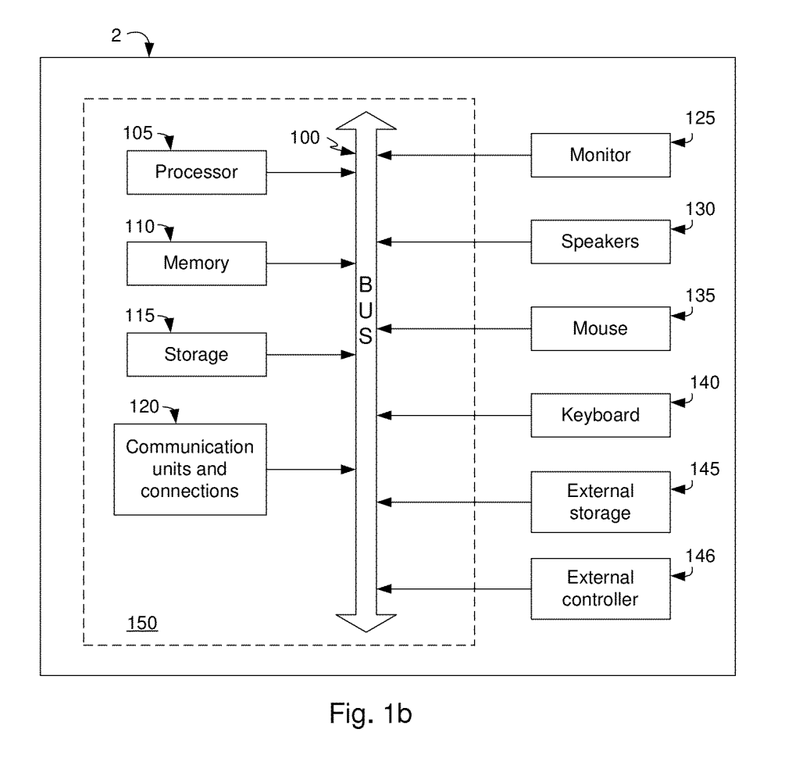
FIG. 1b is an exemplary schematic illustration depicting external and internal components of user system of the present invention.

FIG. 1b schematically illustrates an exemplary of User A 2 system. In one embodiment of the present invention User A 2 computer including BUS line 100 wherein hardware units are connected to it. These hardware units include processor unit 105, memory 110, storage 115, communication units plus connections 120, monitor 125, speakers 130, mouse 135, keyboard 140 and external storage 145 if needed to save user A 2 data or getting data.

In another embodiment of the present invent, an External controller 146 connected to internal part 150 of user computer. External controller 146 getting information to activate external devices, which are not part of User A 2 computer. The controller can operate or cause the operation of electrical or electronic devices, for example TV set, radio and the like.

Figure 1C:
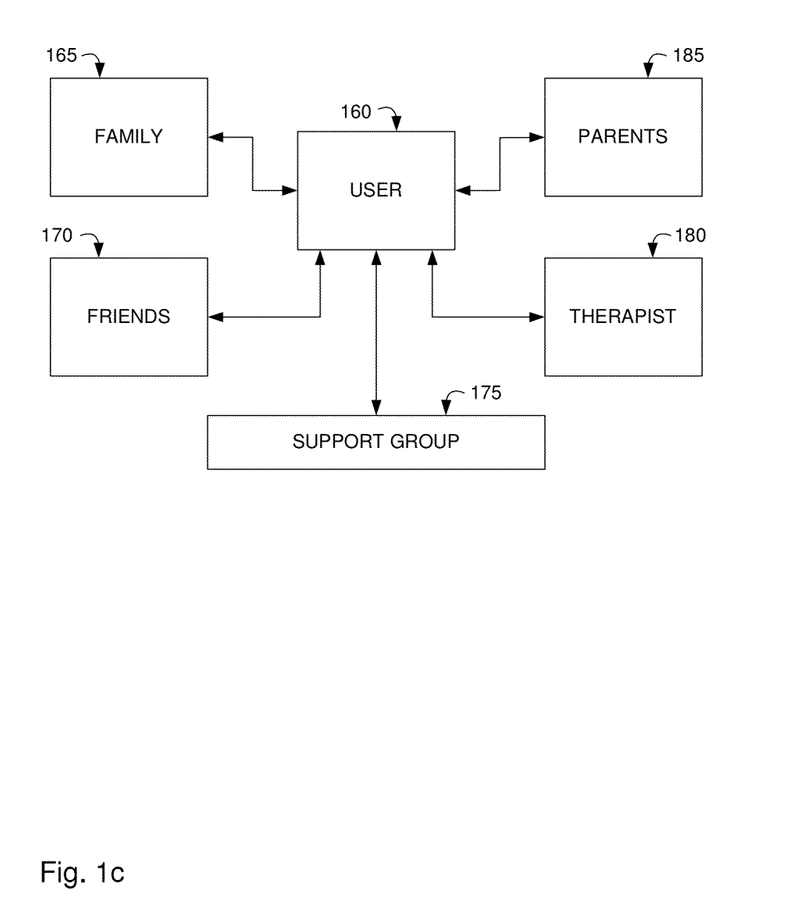
FIG. 1c schematically illustrates exemplary user third parties connections.

FIG. 1c schematically illustrates an exemplary of user 160 third parties connections. User 160 can be one of users describes in FIG. 1a or the like. User 160 can be connected to family 165 elements, friends 170 element, support group 175 element, therapist 180 element and parents 185 element. These surrounding user element connections can be part of a regular activity of the user, which sending and getting digital information. In one embodiment of the present invention, these surrounding element connections are part of the identifying, treatment and weaning of the user's addiction to computer and Internet. Each connected element can be but not limited to a computer, cell phone, a TV that connected to the Internet and the like.

Figure 2:
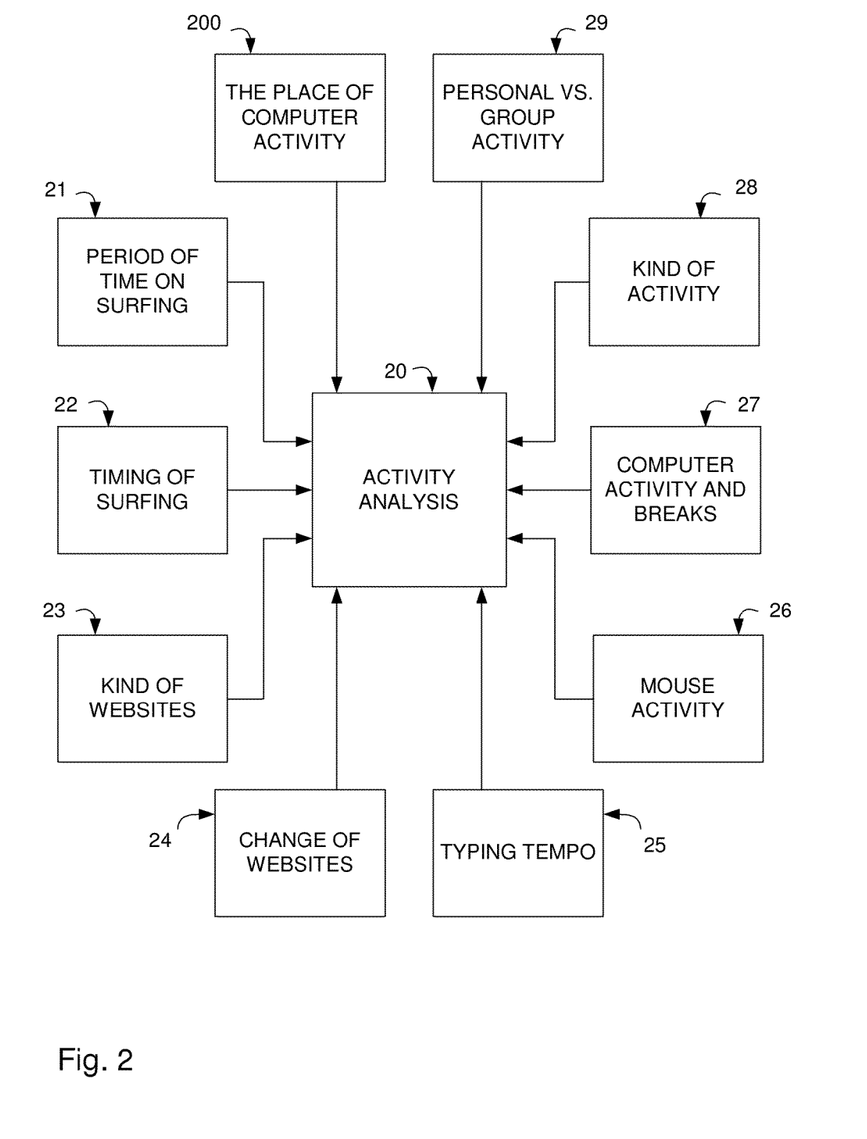
FIG. 2 schematically illustrates exemplary data parameters of the activity analysis.

FIG. 2 is a schematic illustration depicting data parameters which affecting the analysis activity 20 by user activity of surfing the web or other Internet activities or the like activities. These activities may include but not limited to participating in Internet chat rooms, surfing in websites, sending and receiving emails and participating in Internet forums or playing games or offline games and the like. Activity analysis 20 collects data of operation from user personal computer or other device including operating system. Time period of surfing 21 is one parameter, affecting Activity Analysis 20. Activity Analysis can be done in a specific software program as in one embodiment of the present invention or part of a designated program, which software is added to, on a third party computer or specific website.

Another parameter of the analysis is Timing of surfing 22. Surfing the Internet at different hours of the day, are not the same, afternoon surfing has different effect versus night surfing. Internet usage is very common in use, and a possibility to be addicted is growing along the last years.

Kind of websites 23 parameter is affected by the dangerous rate of each website. Surfing Wikipedia™ website is different from surfing porno sites or even social sites.

Change of websites 24 parameter is telling how often the user is changing and moving from one activity to another and which websites he prefer.

Another parameters, which affect the analysis, are coming from peripheral units, such as keyboard and mouse. Typing tempo 25 parameter reflect the operation of the keyboard. The tempo of the typing can show also physiological aspects of the user. Mouse activity 26 parameter is also showing physiological elements of the user with the regular mouse operation.

Computer activity and breaks 27 parameter is showing how often the user is doing breaks or stop using the computer. Which kind of activity the user is using his device is also affected this parameter. Is the user working on documents per his job, or surfing the net or even playing online games or the like, are examples of activities in one embodiment of the present invention which affecting this parameter.

Kind of activity 28 parameter is showing what is the specific activity the user is doing on the computer. Is the user working on word processor for creating documents, working on spreadsheets, doing presentations or just surfing? Is the surfing period is at work, for work or for pleasure.

Personal versus group activity 29 parameter is showing which kind of activity the user is doing. Is the user connecting to other users online or is he working privately on the computer.

The place of computer activity 200 parameter depends on the place user operate the computer or other software-based devices. The activity can be in one embodiment of the present invention at home, at work or other places the like. Operation can be at same device mostly or on some devices in parallel or one by one. Each device can be but not limited to a computer, cell phone, a TV that connected to the Internet and the like.

All parameters describe here are kind of examples and not limited to be all or part of them affecting the analysis. While other parameters can be part of the analysis and not presented here.

Figure 3A:
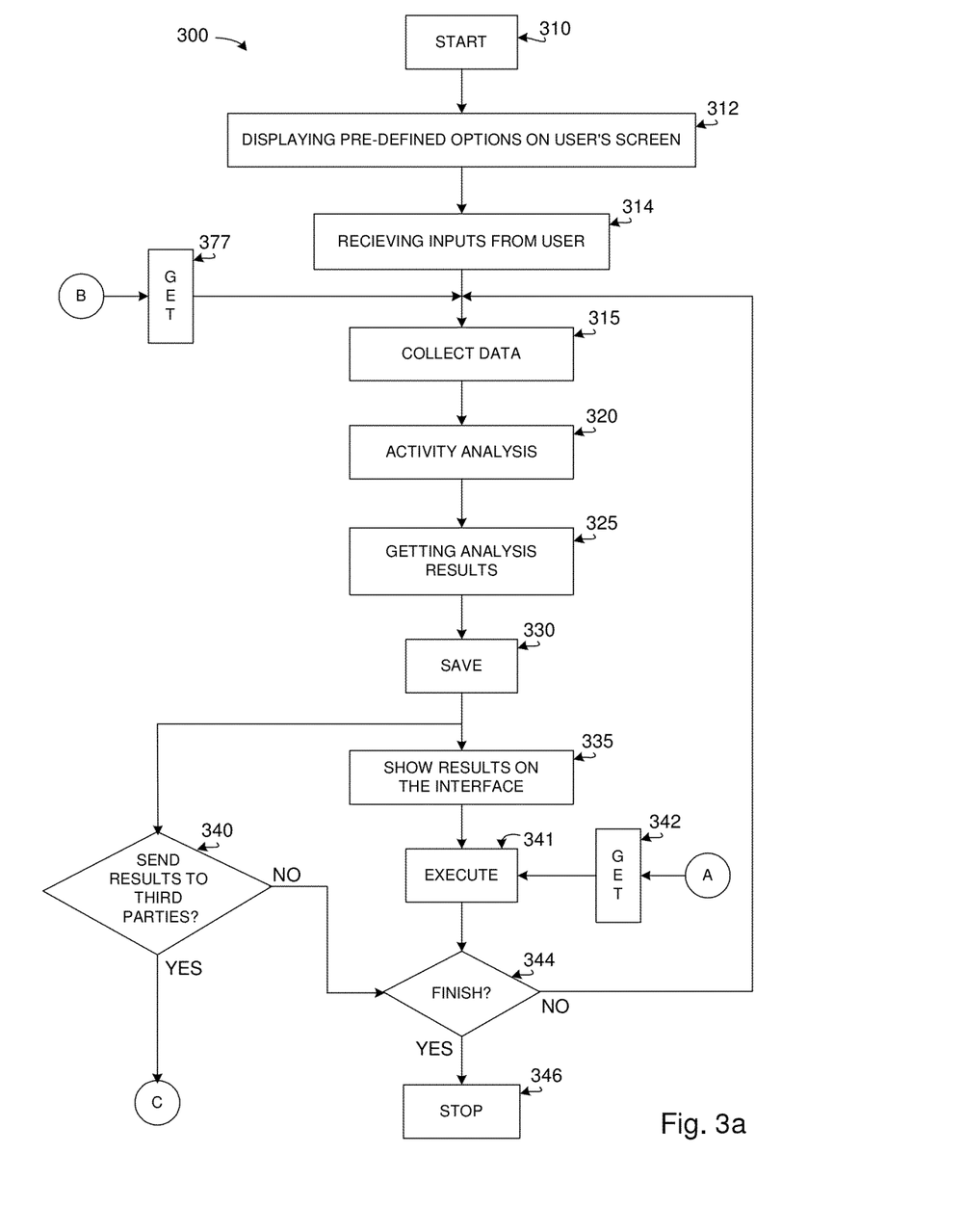
FIGS. 3a and 3b are schematic illustrations depicting the method of identify, treatment and weaning from Internet and computer addiction.
Figure 3B:
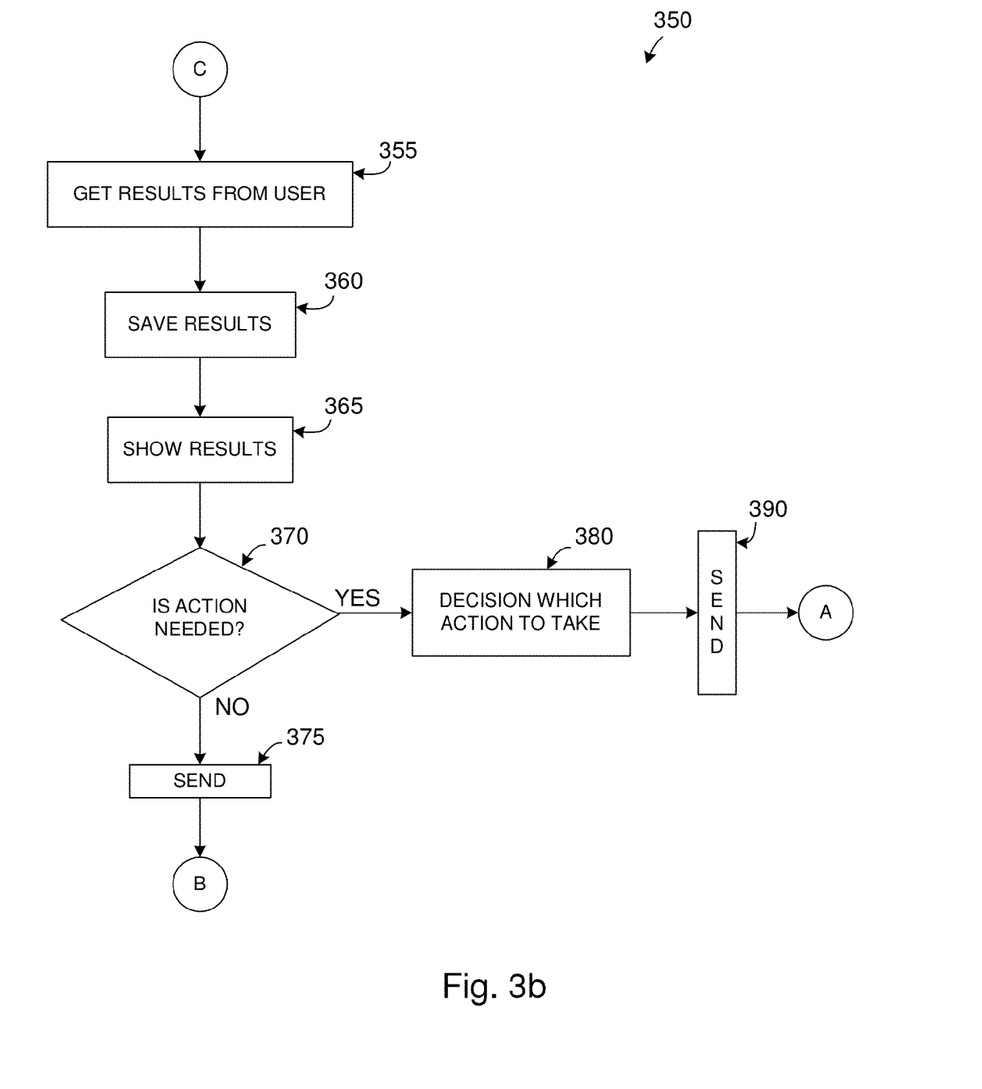

FIGS. 3*a* and 3*b* are exemplary schematic illustrations depicting a method of identify, treatment and weaning from Internet and computer addiction. FIGS. 3*a* and 3*b* are including two parts: FIG. 3*a* presenting user 300 side, while FIG. 3*b* presenting third party 350 side.

Figure 4:
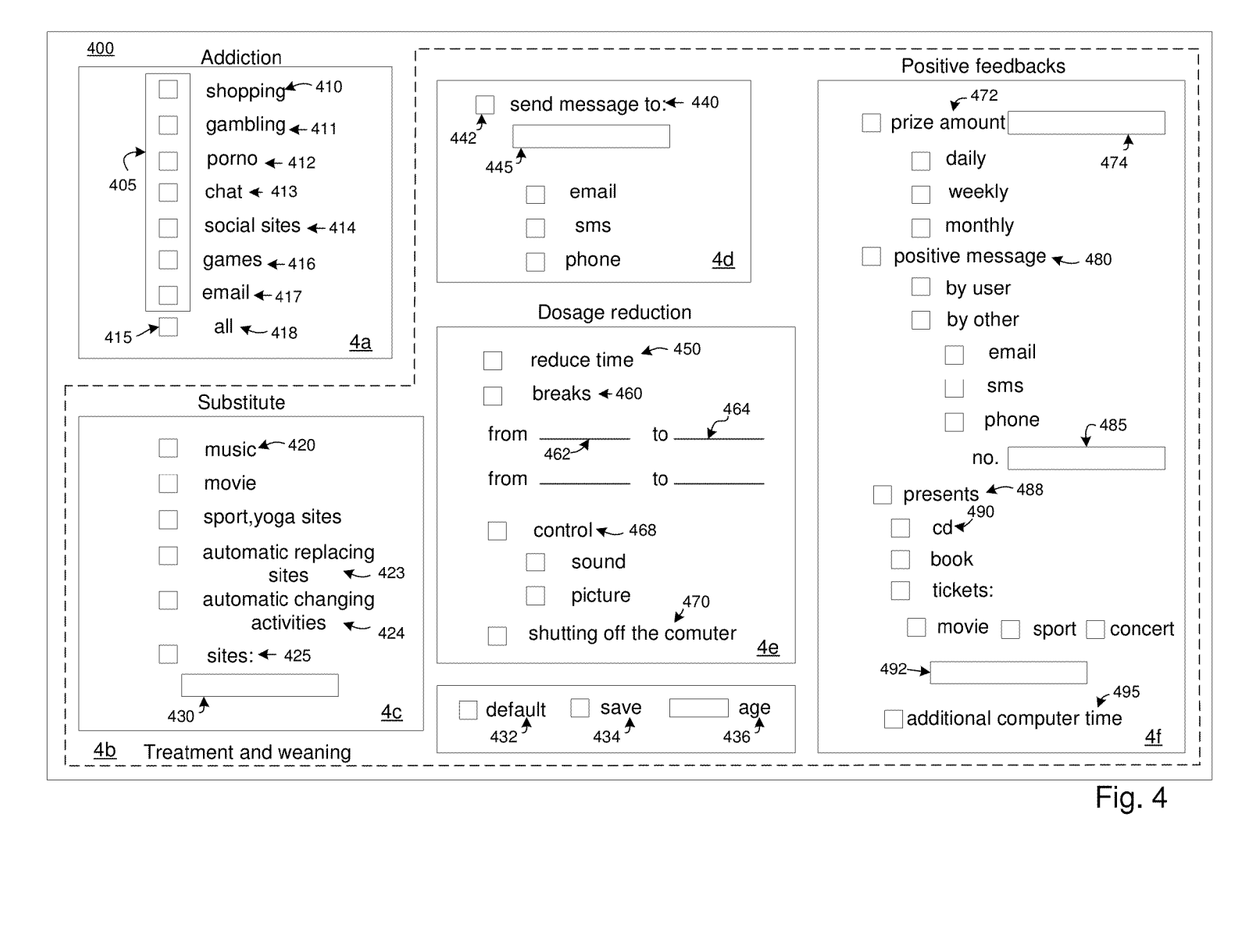
FIG. 4 schematically illustrates exemplary user interface screen of the present invention.

In step start 310 the user starts operate his user A 2 computer. In step 312 pre-defined options such as addiction to shopping 410, gambling addiction 411, porno addiction 412 and the like, are displaying on user's screen 400. In step 314 user is checked or file, on his interface screen 400, his appropriate options according his addicted behavior and personal data. On one embodiment, if shopping addiction has to prevent, check-box 405 has to be checked.

In step 315, while user is operating his computer 2, data is collected to achieve information of the user Internet and computer activity. Examples of this data parameters presents at FIG. 2 and including for example, time of surfing 21, kind of websites 23, mouse activity 26 and the rest which described as example In FIG. 2.

These data parameters are input parameters for activity analysis 320 step. On one embodiment a mathematical analysis is done to get numerical results. User activity can vary from common activity, to a wide activity when he is spending a lot of time surfing the net. The kind of websites he is visiting can vary and how long he spent surfing, jumping from site to site or surf mainly specific sites. This analysis can identify if the user is an Internet or computer addicted or he doesn't. In step 325 getting analysis results from the processing unit and saving it in step 330. These stored analyzed results will be used on the next calculations and statistical manipulation of analysis activity 320. In step 335 the results of the analysis are showing on user interface. User interface can be a computer screen, TV screen, cellular phone screen and the like. An icon, blinker, sign or any other indicator can show the results.

In step 341 an executable operation or operations are acting according the results of user activities and user's inputs 314 of pre-defined options. For example, the computer can shut off in a small period of time, a movie can start, music could play, a message appears or other options. These acts influence the present and future activities of the user, which is surfing and working on the computer. It is the treatment of changing user habits on using his computer to surf the Internet or using it for other activities.

In step 344 if the user decided to stop working on the computer the process stopped in step 346 or continue to step 315 if there is no action or decision to stop. In step 340 if pre-defined option 440 of mode of operation is to send results to third party 3, 4 or 5 in FIG. 1, results are sending to the third party by a physical line, wireless connection or any other network connection. If in step 340 the pre-defined option of mode of operation is not to send any information to third party, the loop continue to step 344, asking if finish is required, if yes, goes to step 346, if no goes back to step 315, starting another loop.

In FIG. 3*b*, third party user 350 gets the results in step 355 which sent by user 300 in step 340. The results are saved in step 360 and are presented on user interface of the third party unit in step 365. In one embodiment third party user 350 is asked in step 370 if action is needed. User is asked by a message or any indication appearing on his user interface. Another embodiment of the present invention is a pre-defined mode of operation, which automatically acts per the results of user A 2 activity, who is surfing the net or other activity on the computer. This decision how to act is in step 380. The executable action send in step 390 by the Internet or other options such as sms, phone call or the like, to the user 300 step 342, to the execution step 341. If no action is needed per step 370, an optional message is sending in step 375 back to user 300 step 377 or any message or action is operate and the process continue back to step 377.

FIG. 4 schematically illustrates an exemplary of user interface screen 400, which can be in one embodiment of the present invention a website page, in another embodiment can be part of a specific program screen or part of browser software program or added program to a browser. User screen 400 can be presented on any kind of screen, such as but not limited to monitor, LCD monitor, CRT monitor, cell phone screen or TV screen. User screen 400 appears on a user interface or graphic user interface (GUI) including a computer, cell phone, Web TV and the like.

Data which necessary for operating the present invention is inserting by the user including personal data such as age, gender and the like, which added to a pre-defined default data status, which inserted by the manufacturer of the software. This data is divided to some categories: data that give information of user addiction which be inserting to the addiction 4a part or already appears by default in this category. Data that inserted or appears by default for treatment and weaning of user addiction is inserted or being by default at treatment and weaning 4b part. Treatment and Weaning 4b is including parts: substitute 4c part, sending messages 4d part, dosage reduction 4e part and positive feedback 4f part. In the addiction 4a part, checkboxes 405 is checked according to the kind of Internet addiction to be implemented in the present invention software. Is it shopping 410 addiction? gambling 411, porno 412, chat 413, social sites 414, games 416 or email addiction 417. Checkboxes 405 can be checked in any kind of addiction possibilities.

If checkbox 415 all addictions 418 is checked, means that all kind of addictions 410-414 and 416-417 are activating.

Substitute 4c part is substitute activities offer for the user to change his routine usage of the computer. These activities can be for example by user choice, by default or automatically by the software of the present inventions. Substitute activities 4c can be one or more activities such as added relaxing or other kind of music from any kind of sources from the web, CD, external from user computer or internal. Replacing user current activity by showing a movie from any kind of source, replacing current site to another one from any kind of sports, yoga or other pleasure site. This replacement of sites can be by user choice, by default or automatic 423 by user computer or other device he uses. This automatically action which done by the software of the present invention, can tells the user ahead of time about this action or it can be immediate and change his operation to more relaxing and less addicted sites. Automatic changing activities 424 checkbox, when checked, changes automatically user activity to other possibilities to operate user computer or any other device he used. Those automatic activities including but not limited to listening to music, see a movie, surfing another site, taking a break from the computer, sending messages, getting messages, doing some sport exercises and the like. The user has a possibility to enter to a list of sites 425 to the type entry rectangle 430. When user addicted activity is reached high level of exposure to addicted sites or operation as calculated by the present invention, an option of sending massage 4d to third party existed. This action of sending massages to third party is part of the treatment from Internet addiction and it is one embodiment of the present invention.

User checked checkbox 442 to send massages 440 with some options of sending: email, sms, phone call and the like. The person who will get the information is typed in the enter rectangle 445. This person can be apparent on one embodiment, friend, therapist, doctor, support group or specific website.

Dosage reduction 4e part including checkboxes to be checked if decided to reduce Internet surfing activities and other computerized activities. It includes reduction time of activity 450, taking breaks 460 and schedule of taking breaks 462 and 464 for typing the time, period of time or hours of activity or breaks. Another option of the present invention for dosage reduction is by controlling 468 the sound and picture the user get. Sound can be controlled to be louder or silent, picture can be controlled to be brighter or darker, smaller size or bigger size. These acts affect user emotions. Emotions can be relaxed or if the program execute differently, it can be a sign to take a break or even shutting the computer for a while. Last option is reduce the dosage completely by shutting off the computer 470 or other device, which the user is using to operate the present invention.

Very important part of weaning from any kind of addiction and from Internet addiction particularly is in giving positive feedbacks 4f to the Internet addicted user or computer addicted one.

Prizes 472 can be given to the user, money prize with amount 474, given daily, weekly or monthly, or other presents 488. The presents 488 could be one of the following but not limited to: compact disk 490, a book, tickets to a movie or to a sport game, to a concert and the like. The user or others can control of sending positive massages 480. It is advantage that the user can act privately or he can decide whether he wants to involve third parties sending him messages.

Entry type rectangle 492 is the place to type the choices. If the user is no more addicted for example, to the Internet, he can get additional computer time 495 in the future.

Default 432 option and checkbox, is operate to change pre-defined checkboxes on/off positions, and to choose new default on/off positions for the checkboxes according user decisions. Save 434 checkbox is operating to save all positions of checkboxes. User's age is typed into the type entry rectangle 436 to affect addictive analyzing according user's age.

Figure 5:
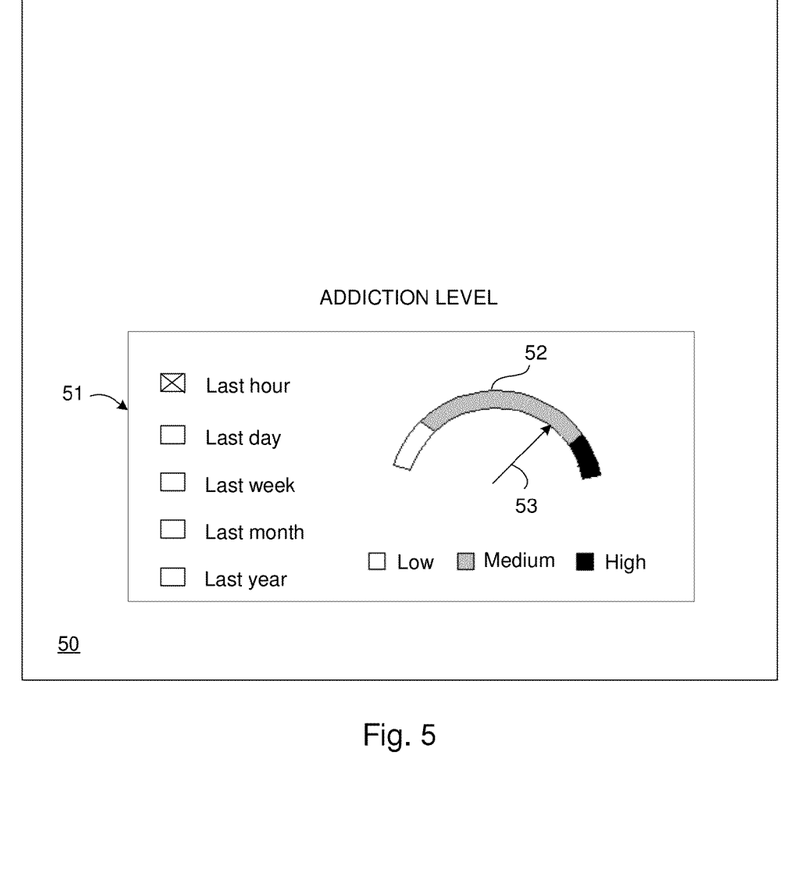
FIG. 5 is a schematic illustration depicting one embodiment of addiction level indicator according to the present invention.

FIG. 5 is a schematic illustration depicting an exemplary of an indicator 51 of addiction level to the Internet or other addicted possibilities, which appearing on user's computer screen 50 or the like. Indicator 51 is including but not limited to scale 52 and arrow 53, which pointed to the value of the addiction level. Level of addiction is a function of data parameters presenting in FIG. 2. On one embodiment, period of time surfing the net is one parameter. These parameters are inputs to the activity analysis 20 operation. The result of the activity analysis 20 operations is the input of addiction indicator 51. The addiction indicator can show the level of addiction along some periods of time, such as at the last minute, last hour, last day, last week, last month or even currently. Checking a chosen checkbox chooses one of these options.

Figure 6A:
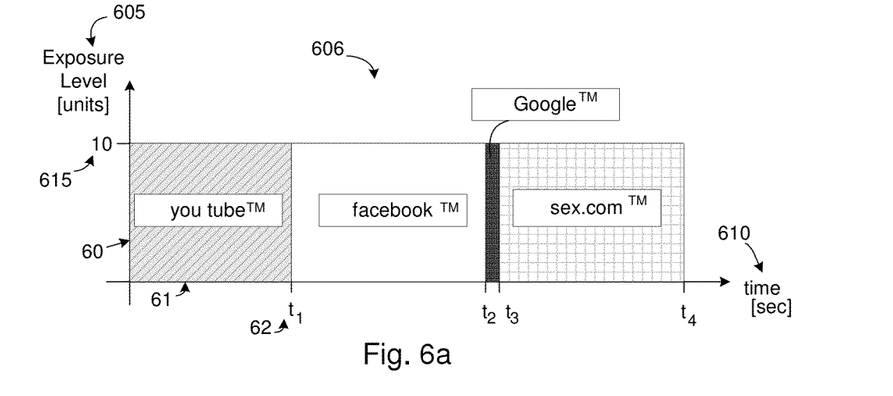
FIG. 6a to FIG. 6e are schematic illustrations depicting embodiments of websites Exposure Level graphs.

FIG. 6a is a schematic graph 606 depicting an exemplary of addiction level that a user can be exposed during surfing the Internet. In one embodiment Addiction level is a function of two parameters: Exposure Level 605 and time 610. In one embodiment of the present invention activity analysis 20 mathematically calculated the area of the graph 606. It is the area below the graph of Exposure level 605 per time 610. In the graph 606, the user surf in Youtube™ site until $t_1$ 62, at Facebook™ between $t_1$ to $t_2$, at Google™ between $t_2$ to $t_3$ and Sex.com™ until $t_4$.

In this example the addiction level can be exemplary calculated but not limited to:

$$\text{Addiction level} = 10*t_1 + 10*(t_2-t_1) + 10*(t_3-t_2) + 10*(t_4-t_3)$$

Figure 6B:
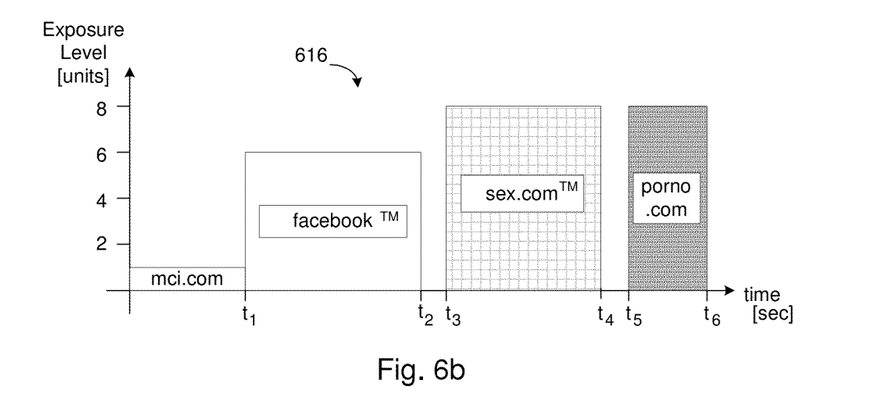

FIG. 6b is another schematic graph 616 depicting an exemplary of addiction level that a user can be exposed during surfing the Internet. In this example websites have different exposure level depending of the risk to be addicted by them. For example, Mci.com™ is at exposure level 1, Facebook™ at exposure level 6, Sex.com™ has exposure level 8 and Porno.com™ has exposure level 8 too. In this example the addiction level can be exemplary calculated but not limited to:

$$\text{Addiction level} = 1*t_1 + 6*(t_2-t_1) + 8*(t_4-t_3) + 8*(t_6-t_5)$$

Between the periods $t_2$ to $t_3$ and $t_4$ to $t_5$ the user did not surf so the exposure level is zero.

Figure 6C:
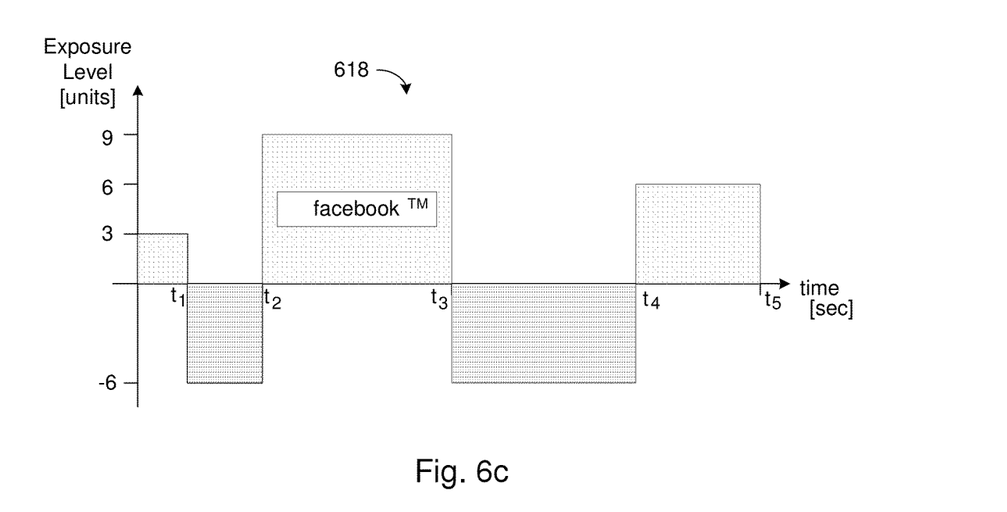

FIG. 6c is another schematic graph 618 depicting an exemplary of addiction level that a user can be exposed during surfing the Internet. The exposure level is getting also negative values which is belonging to breaks from surfing, if actually making breaks by leaving the computer or the like, or doing other activities than surfing the Internet.

Figure 6D:
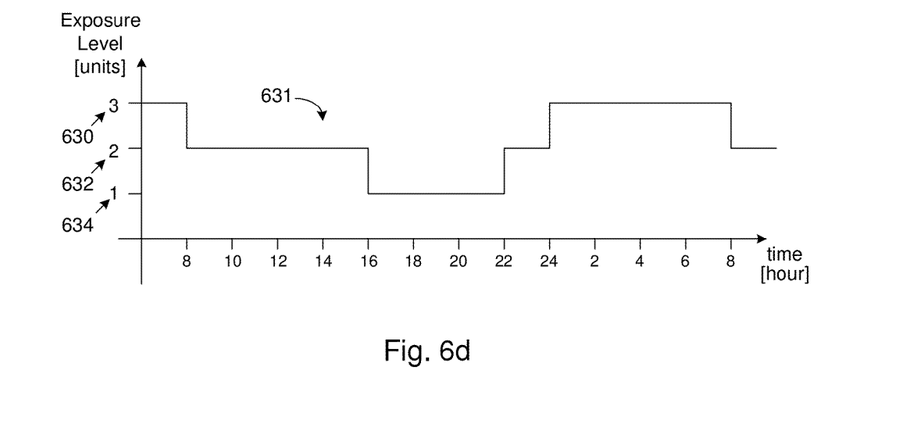

FIG. 6d is schematic graph 631 depicting an exemplary of varying values of Exposure Level depending of what time of the day or night the user is surfing the Internet or having different activity using a computer or other device. Highest level of exposure occurred at night between midnight till 8:00 in the morning. At this period the Exposure level is 3 units 630. Between 8:00 till 16:00 the level is 2 units 632. And at the afternoon till night, meaning between 16:00 till 22:00 the level is 1 unit 634. So surfing in a same site in different hours of the day will change the exposure level according the time of surfing.

Figure 6E:
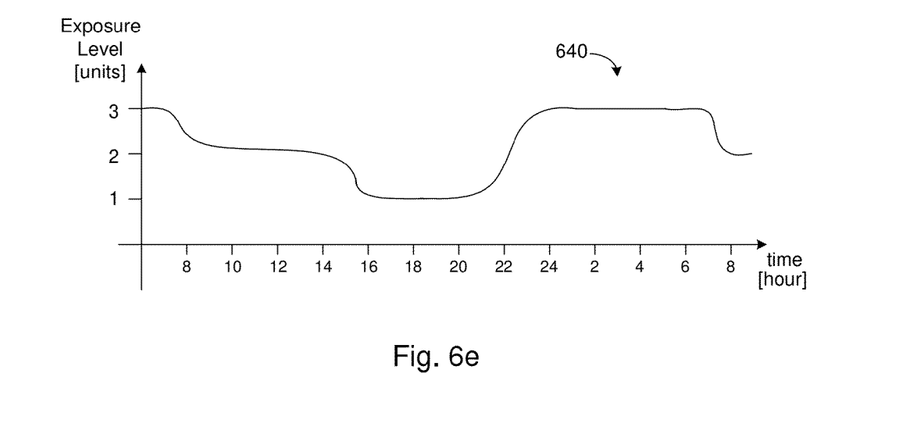

FIG. 6e is schematic graph 640 depicting an exemplary of values of Exposure Level that changing smoothly depending the time of the day and night which user is surfing the Internet or the like. In another embodiment of the present invention, the time is varying depending also of the place of the activity: is it done at home or at work or different place.

Addiction Level calculation that presented here by example can be included but not limited to different calculations, different parameters and different graphs and the like. For example it can be including but not limited to parameters described in FIG. 2: rate of change of websites visited, speed of typing, speed of moving the mouse, personal vs. group activities, kind of activities: chatting, surfing, sending and getting emails, gaming, gambling, online games, online CyberSex and visiting any kind of websites, surfing social websites, kind of software programs operated by any computer, cell phone, TV which connected to network or Internet or other electronic devices, any kind of the like devices: computer, cell phone, TV which connected to network or Internet or other electronic device and the like.

Advantages:

From the description above, a number of advantages of some embodiments of my identifying, treatment and weaning from Internet and computer addiction become evident:

(a) On one embodiment, opposed to parental control methods, which are based on supervising user activity, the present invention is giving the whole responsibility to the user fighting his addiction.

(b) The user doesn't need to bypass the controlled product as done today or to use a different computer or to surf the Internet from a proxy server, if he doesn't agreed in using a controlled product. With the proposed invention, on one embodiment, the whole responsibility is in user hands fighting his addiction, giving him the option to choose which action is needed.

(c) The proposed invention has also the option to involve third parties such as parents, friends, therapists, and support groups helping the user to prevent and to act against the addiction.

(d) The new proposed invention is dealing with all aspects of addiction from identification point, the treatment and the weaning. Starting from a point of choosing which kind of addiction the system will work on, continuing to substitute activities, sending alerts and dosage reduction. Although giving positive feedbacks to the user if he reduced his addiction. These feedbacks even including presents and prizes as part of a weaning process.

(e) The new invention acts for all kind of users, all ages and different gender, in all addictive levels even those who are currently no addictive to the Internet and the computer but with no attention they probably will. It gives them the ability to view their current and past addictive level visually to prevent from the phenomena.

(f) According to the report of Helly Peretz, which mentioned above, 94% of Internet surfers are not addicted to the Internet. The present invention offered them a tool to prevent from addiction. Although, they don't need to be controlled by anyone or by any device and can act privately on their computer or the like without interfering from third parties.

(g) The new system can work off-line or on-line, on a browser or specific software, on a website or any computerized implemented system.

Although the description above contains many specificities, these should not be construed as limiting the scope of the embodiment but merely providing illustrations of some of the presently preferred embodiments.

I claim:

1. A user's self-controlled method for identify, treatment and weaning from Internet and computer addiction, comprising:
    (a) displaying via an interface unit, pre-defined items to be checked by the user, including personal data, and options of treatment and weaning from addiction;
    (b) receiving from the user, via an interface unit, said input items;
    (c) collecting in a memory unit, user's activities on a computer and on a network;
    (d) analyzing graphically, by a processor unit, said user activities in order to calculate a user's addiction level;
    (e) saving in a storage unit, said analyzed activity results;
    (f) presenting visually via the user's interface unit, said user addiction level according to the past and present said activity results;
    (g) executing treatment actions including supporting substitute materials, dosage reduction and positive feedbacks including presents, prizes and positive messages, according to said user addiction level to prevent and reduce addictive behavior;
    (h) executing operations by one or more external controllers to operate one or more external electric and electronic devices, such that the external controller receives its input data from a user's computerized device so that the input data is dependent upon the user's addiction level, as part of his treatment and weaning from Internet and computerized devices;
    (i) taking decisions by said user, according to said user addiction level, whether to involve third parties in getting treatment;
    (j) sending on a network said user's addiction level to third parties;
    (k) presenting visually via third parties' interface units said user's addiction level according to said activity results;
    (l) taking decisions of treatment and weaning by third parties according to said user addiction level;
    (m) sending back via a network third parties' decisions to affect said execution in stage (g).

2. The method according to claim 1 wherein said pre-defined display items are from selectable choices.

3. The method according to claim 1 wherein said pre-defined display items have been selected previously as a default data status, by said third party including one or more of: a manufacturer, a user, a parent, a therapist, a supervisor, for activating a pre-defined status.

4. The method according to claim 1 wherein said user's activities include one or more of: duration of surfing, timing of operation, kind of websites visited by the user, changing between websites and activities, keyboard's typing tempo, mouse activity, computer activity and breaks, kind of activity, personal vs. group activity and the location where the activity on the computer is taking place.

5. The method according to claim 1 wherein said third parties are one or more of: a parent, a friend, a supervisor, a social website, a group therapy, a therapist, a doctor.

6. The method according to claim 1 wherein said decisions include sending execute messages and execute actions for delaying, stopping, or changing said user's computerized device activity, are third parties' decisions only and are not affected by said user decision.

7. The method according to claim 1 wherein said third parties' decisions are being sent via a communication unit.

8. The method according to claim 1 wherein said sending user's addictive level is being sent via a communication unit.

9. The method according to claim 1 wherein said analyzing user activity is a mathematical analysis.

10. The method according to claim 1 wherein said network is the Internet.

11. The method according to claim 1 wherein said network is the Intranet.

12. A computerized system for identify, treatment and weaning from Internet and computer addiction, comprising:
   (a) memory unit for storing identify, treatment and weaning applications of user's addiction to the Internet and a computer;
   (b) processor unit for analyzing user activity of one or more of: duration of surfing, timing of surfing, kind of websites, change of websites, typing tempo, mouse activity, computer activity and brakes, kind of activity, personal vs. group activity, location where the computer activity is taking place, and executing calculations, wherein each said activity is a parameter of at least one function, in order to obtain the user's Internet and computer addiction level results;
   (c) storage unit for storing the said user's addiction level results;
   (d) interface unit for displaying visually the said addiction level results;
   (e) communication unit for getting and sending information of said addiction level and decisions how to act, including at least one of the plurality of getting substitute activities, sending messages, activity dosage reduction, positive feedbacks from and to third parties and for surfing the web;
   (f) one or more of an external controller units for controlling an external electric and electronic devices which is not part of the user's computer, such that the controlling process is per the user's addiction level, as part of his treatment and weaning from Internet and computerized devices.

13. The system according to claim 12 wherein said interface unit is an interface of one or more of: a cellular phone, a smart phone, a PDA, a desktop computer, a laptop computer, a notebook computer, a website.

14. The system according to claim 12 wherein said communication unit is the Internet.

15. The system according to claim 12 wherein said sending and getting of information is according to a pre-defined option.

16. The system according to claim 12 wherein said sending and getting of information is according to a user's decision.

* * * * *